(12) United States Patent
Lichte et al.

(10) Patent No.: US 8,124,737 B2
(45) Date of Patent: Feb. 28, 2012

(54) STABILIZED PREPARATIONS OF SERINE ENDOPEPTIDASES, THEIR PREPARATION AND USE

(75) Inventors: Andrea Lichte, Marburg (DE); Verena Kräling, Burgwald (DE)

(73) Assignee: Seimens Healthcare Diagnostics Products GmbH, Marburg (DE)

( * ) Notice: Subject to any disclaimer, the term of this patent is extended or adjusted under 35 U.S.C. 154(b) by 556 days.

(21) Appl. No.: 11/709,747

(22) Filed: Feb. 23, 2007

(65) Prior Publication Data
US 2007/0231315 A1 Oct. 4, 2007

(30) Foreign Application Priority Data
Feb. 24, 2006 (DE) .................. 10 2006 008 613

(51) Int. Cl.
*A61K 38/48* (2006.01)
(52) U.S. Cl. .................. 530/383; 424/94.64; 435/23
(58) Field of Classification Search .................. None
See application file for complete search history.

(56) References Cited

U.S. PATENT DOCUMENTS

| | | | |
|---|---|---|---|
| 4,918,001 A | 4/1990 | Kolde | |
| 5,308,755 A | 5/1994 | Nesheim et al. | |
| 5,593,968 A | 1/1997 | Turecek et al. | |
| 6,514,940 B2 * | 2/2003 | Romisch et al. | 514/20.1 |
| 6,737,405 B2 | 5/2004 | Roemisch et al. | |
| 2001/0031721 A1 | 10/2001 | Webb et al. | |

FOREIGN PATENT DOCUMENTS

| | | | |
|---|---|---|---|
| AT | EP 0 680 764 | * 11/1995 | |
| DE | 43 25 872 | 8/1994 | |
| EP | 0 216 179 | 4/1987 | |
| EP | 0 292 003 | 11/1988 | |
| EP | 0 680 764 | 11/1995 | |
| EP | 0 702 719 | 3/1996 | |
| EP | 1 153 608 | 11/2001 | |
| WO | WO 90/13320 | 11/1990 | |
| WO | WO 2005/042012 A1 | 5/2005 | |
| WO | WO 2005/058283 | 6/2005 | |

OTHER PUBLICATIONS

Wu et al., Thrombosis Research, 1978, 13(4), pp. 701.*
Bajaj et al., "Simultaneous Purification of Bovine Prothrombin and Factor X", The Journal of Biological Chemistry, vol. 248, No. 22, pp. 7729-7741, (1973).
Carr et al., "Effect of Homo Poly(L-Amino Acids) on Fibrin Assembly: Role of Charge and Molecular Weight", Biochemistry, vol. 28, No. 3, pp. 1384-1388, (1989).
Lindsay et al., "Purification of Recombinant DNA-Derived Factor IX Produced in Transgenic Pig Milk and Fractionation of Active and Inactive Subpopulations", Journal of Chromatography A, 1026, pp. 149-157, (2004).
Wu et al., "Preservation of factor Xa activity," Abstract of Thrombosis Research (1978), 13(4) 701, from Database CA [online] Chemical Abstracts Service, CA Copyright 2007 ACS on STN, XP-002457370.
Donald Voet et al., "Serine Proteases," Biochemistry, 1995, pp. 389-400, 2d Ed., John Wiley & Sons.
J.C. Rau et al., "Serpins in thrombosis, hemostasis and fibrinolysis," Journal of Thrombosis and Haemostasis, vol. 5 (Suppl. 1), pp. 102-115, (Mar. 2007).
V.G.H. Eijsink et al., "Rational engineering of enzyme stability," Journal of Biotechnology, vol. 113, pp. 105-120, (2004).
W. Wang, "Instability, stabilization, and formulation of liquid protein pharmaceuticals," International Journal of Pharmaceutics, vol. 185, pp. 129-188, (1999).

* cited by examiner

*Primary Examiner* — Christopher R. Tate
*Assistant Examiner* — Roy Teller
(74) *Attorney, Agent, or Firm* — Finnegan, Henderson, Farabow, Garrett & Dunner, L.L.P.

(57) ABSTRACT

The invention relates to stabilized preparations of serine endopeptidases which are suitable for use as a test reagent in a diagnostic procedure or for a therapeutic use. As a result of the addition of various additives, the preparations have improved stability and shelf life.

31 Claims, 4 Drawing Sheets

STABILIZED PREPARATIONS OF SERINE ENDOPEPTIDASES, THEIR PREPARATION AND USE

This U.S. non-provisional application claims priority to German Application Serial No. DE 10 2006 008 613.9, filed Feb. 24, 2006, which is incorporated herein by reference in its entirety.

The present invention is in the field of the production of preparations (compositions) which are intended for therapeutic use or for use as a test reagent in a diagnostic process and in particular relates to preparations of serine endopeptidases, which as a result of the addition of various additives have improved stability and shelf life.

Proteases (synonym: peptidases) are enzymes which have the ability to hydrolyze peptide bonds. The stability of preparations which contain proteases is one of the most important parameters which traditionally determine the possibilities of commercial application of proteases in industrial processes. The stability of proteases must be taken into consideration during their production, isolation, purification, storage and finally also in the use of the product which contains the protease. In order to guarantee an adequate biological activity over an acceptable period of time, preparations which contain a protease, like many other protein products, are customarily stored under refrigerated conditions or even freeze-dried.

For the stabilization of enzymes or proteins in general, different strategies are known. The aim of stabilization strategies is essentially to avoid denaturation of the protein. The native structure of a protein is in general the protein conformation which is the most stable (conformation having the lowest energy) and is the conformation that the protein assumes in its cellular environment or the conformation in which the isolated protein has its maximum biological activity. The denaturation of a protein describes the process which leads to a change in the three-dimensional native protein structure whereby the amino acid sequence (primary structure) remains unchanged. A change in the molecular structure of an enzyme can have effects on the correct arrangement of its active center and lead to inactivation of the enzyme. The stabilization of a protein molecule or of a preparation which contains protein molecules is understood by the protein chemist as meaning the avoidance of conformational changes within the protein molecule. Stabilization consequently leads to retention of the native structure and thus also to preservation of the biological activity. Conversely, from a determination of the activity of an enzyme, for example of a protease, conclusions about the integrity of its structure can be drawn.

In connection with medicinal products or products for in vitro diagnosis, stability is customarily understood as meaning that a product keeps its necessary specifications over the period of its storage or its use, for example, in the most favorable case, it retains the properties and characteristics as at the time of its production.

To predict the stability of a protein preparation, accelerated stability studies are often carried out. These studies are designed such that the chemical or physical degradation of a protein product is accelerated under increased stress conditions (e.g. elevated temperature, high atmospheric humidity, light, shaking). From the stability investigations under increased stress conditions, conclusions can be drawn about the actual long term stability of a protein. This conclusion can be based on experience with similar protein products and/or using the Arrhenius equation or other established mathematical models.

Usually, the rate of degradation processes in protein solutions is slow under typical storage conditions (e.g. +2 to +8° C.). At elevated temperatures, movements of molecules and their oscillation amplitudes increase. As a result, molecular collisions occur more frequently and molecule degradation increases. The relationship between reaction rate and temperature was summarized by van't Hoff in the reaction rate-temperature rule. This rule states that an increase in temperature by 10 Kelvin results in an increase of the reaction rate by two to four times. Mathematically and physically, this phenomenon is described by means of the Arrhenius equation, according to which the temperature dependence of the reaction rate is an exponential function.

The addition of stabilizing agents to a protein formulation is often the means of choice in order to improve the stability of a protein. However, up to now no one has succeeded in developing a universal stabilization strategy which can be used for all proteins. It is speculated that the protective effect of a stabilizing substance is dependent on the specific structural properties of the protein to be stabilized. Accordingly, stabilizing substances for specific proteins are selected principally with the aid of empirical studies. Possible stabilizers used are, inter alia, antioxidants or reducing agents for the prevention of oxidative degradation, proteinase inhibitors for the prevention of proteolytic processes, chelating agents for the exclusion of heavy metal ions, or bacteriostatics and fungicides for the avoidance of microbial growth. Losses of activity owing to physical effects such as adsorption, denaturation by surfaces, heat denaturation, drying and repeated freezing and thawing can frequently be markedly reduced by addition of glycerol, carbohydrates, amino acids, hydrophilic polymers or inert proteins. Human serum albumin (HSA), bovine serum albumin (BSA) or ovalbumin are often used as stabilizing agents for freeze-dried proteins. A disadvantage of the use of protein additives of this type is possible contamination with biologically active materials, such as, for example, proteases or protease inhibitors, which negatively influence the biological activity of the protein to be stabilized. Moreover, the addition of large amounts of albumins in most cases excludes the possibility of subsequent physicochemical analysis of the desired protein.

The present invention was based on the object of making available a process for the stabilization of serine endopeptidases.

Within the meaning of the present invention, a serine endopeptidase is an enzyme which has the following structural or functional characteristics:

I. A serine endopeptidase is always a hydrolase which cleaves peptide bonds;
II. this activity depends on a group of amino acid residues which, related to the primary structure of the enzyme, can be far away from one another, but are approximated by a higher-ranking structure in the active, catalytic center ("catalytic triad"), one of these amino acid residues always being a serine residue;

III. in contrast to the "exopeptidases", which cleave a polypeptide from the C or N terminus and, depending on their specificity, release tripeptides, dipeptides or alternatively individual amino acids, a serine endopeptidase cleaves peptide bonds which are situated within a protein or polypeptide;

IV. a serine endopeptidase is irreversibly inhibited by phenylmethylsulfonyl fluoride (PMSF), since PMSF sulfonylates the serine residue in the active center;

V. a serine endopeptidase is irreversibly inhibited by diisopropylfluoro phosphate (DFP), since DFP phosphorylates the serine residue in the active center.

According to the International Enzyme Classification System (=E.C.), which was developed by the International Union of Pure and Applied Chemistry (IUPAC) and the International Union of Biochemistry, each enzyme is assigned an E.C. number consisting of four figures (see also www.chem.qmul.ac.uk/iubmb/enzyme).

Serine endo-peptidases which have the abovementioned characteristics are summarized in enzyme class E.C. 3.4.21. The individual members of this class in each case contain one additional number. The presently known members of the enzyme class of serine endopeptidases E.C. 3.4.21 are listed in table 1.

TABLE 1

| E.C. 3.4.21.1 | chymotrypsin |
|---|---|
| E.C. 3.4.21.2 | chymotrypsin C |
| E.C. 3.4.21.3 | metridin |
| E.C. 3.4.21.4 | trypsin |
| E.C. 3.4.21.5 | thrombin |
| E.C. 3.4.21.6 | blood clotting factor Xa |
| E.C. 3.4.21.7 | plasmin |
| E.C. 3.4.21.9 | enteropeptidase |
| E.C. 3.4.21.10 | acrosin |
| E.C. 3.4.21.12 | alpha-lytic endopeptidase |
| E.C. 3.4.21.19 | glutamyl endopeptidase |
| E.C. 3.4.21.20 | cathepsin G |
| E.C. 3.4.21.21 | blood clotting factor VIIa |
| E.C. 3.4.21.22 | blood clotting factor IXa |
| E.C. 3.4.21.25 | cucumisin |
| E.C. 3.4.21.26 | prolyl oligopeptidase |
| E.C. 3.4.21.27 | blood clotting factor XIa |
| E.C. 3.4.21.32 | brachyurin |
| E.C. 3.4.21.34 | plasma kallikrein |
| E.C. 3.4.21.35 | tissue kallikrein |
| E.C. 3.4.21.36 | pancreatic elastase |
| E.C. 3.4.21.37 | leucocyte elastase |
| E.C. 3.4.21.38 | blood clotting factor XIIa |
| E.C. 3.4.21.39 | chymase |
| E.C. 3.4.21.41 | complement factor C1r |
| E.C. 3.4.21.42 | complement factor C1s |
| E.C. 3.4.21.43 | C3/C5 convertase (classical) |
| E.C. 3.4.21.45 | complement factor I |
| E.C. 3.4.21.46 | complement factor D |
| E.C. 3.4.21.47 | C3/C5 convertase (alternative) |
| E.C. 3.4.21.48 | cerevisin |
| E.C. 3.4.21.49 | hypodermin C |
| E.C. 3.4.21.50 | lysosymal endopeptidase |
| E.C. 3.4.21.53 | endopeptidase La |
| E.C. 3.4.21.54 | gamma-renin |
| E.C. 3.4.21.55 | venombin Ab |
| E.C. 3.4.21.57 | leucyl endopeptidase |
| E.C. 3.4.21.59 | tryptase |
| E.C. 3.4.21.60 | scutelarin |
| E.C. 3.4.21.61 | kexin |
| E.C. 3.4.21.62 | subtilisin |
| E.C. 3.4.21.63 | oryzin |
| E.C. 3.4.21.64 | proteinase K |
| E.C. 3.4.21.65 | thermomycolin |

TABLE 1-continued

| E.C. 3.4.21.66 | thermitase |
|---|---|
| E.C. 3.4.21.67 | endopeptidase So |
| E.C. 3.4.21.68 | tissue plasminogen activator |
| E.C. 3.4.21.69 | protein C (activated) |
| E.C. 3.4.21.70 | pancreatic endopeptidase E |
| E.C. 3.4.21.71 | pancreatic elastase II |
| E.C. 3.4.21.72 | IgA-specific serine endo-peptidase |
| E.C. 3.4.21.73 | urokinase plasminogen activator |
| E.C. 3.4.21.74 | venombin A |
| E.C. 3.4.21.75 | furin |
| E.C. 3.4.21.76 | myeloblastin |
| E.C. 3.4.21.77 | semenogelase |
| E.C. 3.4.21.78 | granzyme A |
| E.C. 3.4.21.79 | granzyme B |
| E.C. 3.4.21.80 | streptogrisin A |
| E.C. 3.4.21.81 | streptogrisin B |
| E.C. 3.4.21.82 | glutamyl endopeptidase II |
| E.C. 3.4.21.83 | oligopeptidase B |
| E.C. 3.4.21.84 | limulus clotting factor C |
| E.C. 3.4.21.85 | limulus clotting factor B |
| E.C. 3.4.21.86 | limulus clotting enzyme |
| E.C. 3.4.21.87 | omptin |
| E.C. 3.4.21.88 | repressor LexA |
| E.C. 3.4.21.89 | signal peptidase I |
| E.C. 3.4.21.90 | togavirin |
| E.C. 3.4.21.91 | flavirin |
| E.C. 3.4.21.92 | endopeptidase Clp |
| E.C. 3.4.21.93 | proprotein convertase 1 |
| E.C. 3.4.21.94 | proprotein convertase 2 |
| E.C. 3.4.21.95 | snake venom factor V activator |
| E.C. 3.4.21.96 | lactocepin |
| E.C. 3.4.21.97 | assemblin |
| E.C. 3.4.21.98 | hepacivirin |
| E.C. 3.4.21.99 | spermosin |
| E.C. 3.4.21.100 | pseudomonapepsin |
| E.C. 3.4.21.101 | xanthomonapepsin |
| E.C. 3.4.21.102 | C-terminal processing peptidase |
| E.C. 3.4.21.103 | physarolisin |

The majority of serine endopeptidases are of animal or human origin, are secreted and have an N-terminal signal peptide. The serine endopeptidases which have such an N-terminal signal peptide are initially synthesized as precursors having an N-terminal propeptide. In the course of the activation of such a serine endopeptidase, the N-terminal propeptide is cleaved, although complete cleavage of the propeptide is not always necessary for activation, in that in some cases the propeptide after its cleavage remains attached to the heavy chain of the protease through disulfide bridges. Nonetheless, the cleavage of the precursor leads to a structural change within the protein molecule, whereby the catalytic center of the protease is converted to the active state.

The serine endopeptidases also include, inter alia, the blood clotting factor II (F II), factor VII (F VII), faQtor IX (F IX), factor X (F X), factor XI (F XI) and factor XII (F XII). In the activated form, the factors are identified by the appendix "a": factor IIa (F IIa, thrombin), factor VIIa (F VIIa), factor IXa (F IXa), factor Xa (F Xa), factor XIa (F XIa) and factor XIIa (F XIIa). The present invention will be illustrated below as exemplified by the blood clotting factors, without, however, the scope of the invention being restricted to this group.

Preparations of isolated or enriched blood clotting factors are needed both for therapeutic and for diagnostic purposes. In the treatment of diseases caused by a congenital or acquired deficiency of one or more blood clotting factors, patients are treated with preparations which contain the missing blood clotting factor or factors in concentrated form. In this case, the blood clotting factors are a constituent of a pharmaceutically acceptable preparation. In the field of diagnostics, blood clotting factors, preferably activated blood clotting factors, are used as reagents for quantitative or qualitative determination or detection of a biological activity or of an analyte in a patient sample. For example, reagents which contain F Xa or thrombin are used in chromogenic test procedures for the determination or detection of antithrombin or heparin.

In relation to test kits, reagents or therapeutic products, it is particularly desirable to make the individual components of the test kit, the reagents or the products which are intended for therapeutic administration available as ready-to-use liquid preparations. A supply of ready-to-use liquid preparations avoids additional working steps, such as, for example, the reconstitution of lyophilized products, and reduces sources of error, such as, for example, inadequate dissolution of a substance, use of an incorrect solvent or solvent volume, and contamination in the preparation of solutions or suspensions of freeze-dried powder. These errors can have an adverse effect on the quality and safety of the entire test procedure. Also, not to be underestimated, is the health risk for patients which can result from the administration of a wrongly reconstituted therapeutic. A particularly important criterion in the development of liquid test reagents or liquid pharmaceutical products is a shelf life that is as long as possible (at least several months) in the liquid state under storage conditions such as, for example, at room temperature between +15 and +25° C. or at refrigerator temperatures between +2 and +8° C.

The provision of ready-to-use, long-term-stable liquid preparations which contain an active enzyme, such as, for example, an active blood clotting factor, is particularly problematical, since many active enzymes are characterized by inherent instability. For instance, activated F Xa in comparison to inactive F X is a labile enzyme, consequently the catalytic activity of purified F Xa decreases with the storage period. For this reason, reagents which contain an activated blood clotting factor, such as, for example, thrombin or FXa, have been provided up to now mainly in lyophilized form and reconstituted shortly before use by dissolving in a suitable solvent, such as water or buffer, or they are stored in the deep-frozen state and only thawed shortly before use.

From the literature, blood clotting factor preparations are known which are stabilized by addition of various additives. For instance, it is reported for purified bovine F Xa that for F Xa dissolved in water stabilization for at least five months is achieved by the addition of 50% (v/v) glycerol and storage at −20° C., while an F Xa preparation in imidazole buffer stored at +4° C. only has 90% of the original activity after one week [see right column on page 7736 in Bajaj, S. P. & Mann, K. G. (1973) Simultaneous purification of bovine prothrombin and Factor X. J. Biol. Chem. 248, 7729-7741]. In DE 43 25 872 C1, a virus-inactivated F Xa preparation is described, which is alternatively treated with sucrose or with human albumin, but lyophilized for long-term stabilization. It was not possible to observe any change in the activity of F Xa over a storage period of six weeks at +37° C. In EP 680 764 A2, a process for the preparation of virus-inactivated protein preparations is described in which the proteins to be stabilized, such as, for example, F Xa, are associated with lipid vesicles, while no stabilizing additives are used. Patent document EP 1 153 608 A1 describes a protein solution which contains one or more blood clotting factors and which is protected against a loss of activity during pasteurization by the addition of stabilizers. The addition of saccharides and/or of amino acids from the group arginine, lysine, histidine, phenylalanine, tryptophan, tyrosine, aspartic acid and its salts and glutamic acid and its salts is described as stabilizing.

The present invention was based on the object of making available a preparation stable for a long term in the liquid state which contains a serine endopeptidase.

The object is achieved by making available the processes and articles according to the invention which are described in the claims.

The present invention provides a preparation which contains at least one serine endopeptidase, the serine endopeptidase being present in the preparation in the desired purity and concentration. Preferably, the serine endopeptidase is a purified serine endopeptidase. A purified serine endopeptidase can be obtained from organic raw material by any suitable process known to the person skilled in the art. Such organic material includes materials in which the serine endopeptidase occurs naturally or has been produced by genetic engineering. Depending on the desired purity of the serine endopeptidase, purification processes can be used which make possible the separation of impurities such as carbohydrates, lipids, nucleic acids, proteins and/or other biomolecules. Raw materials for the obtainment of a serine endopeptidase can be, for example, animal or human tissues or body fluids (e.g. blood, plasma, serum, lymph fluid), supernatants or lysates of animal or human cell cultures, or cultures of eukaryotic cells or of microorganisms, such as bacteria or fungi, which express a recombinant serine endopeptidase. Examples of processes which, as is well known, are used for the purification of proteins, are chromatographic separation processes, such as ion exchange, gel filtration, hydrophobic interaction or affinity chromatography. In addition, preparative gel electrophoresis, preparative isoelectric focusing, chromatofocusing, precipitation and ultracentrifugation can also be used for the purification of proteins from a protein extract.

The present invention relates to a preparation which contains at least one serine endopeptidase and additionally either a) ammonium acetate ($CH_3COONH_4$) or b) at least one polyamino acid or c) glycerol together with at least one amino acid from the group consisting of aspartic acid and its salts, glutamic acid and its salts, histidine and glycine, or d) any desired combination of the additives a) b) and c).

It has been found that the sole addition of a) ammonium acetate, the sole addition of b) at least one poly amino acid, the sole addition of c) glycerol together with at least one amino acid from the group consisting of aspartic acid and its salts, glutamic acid and its salts, histidine and glycine, and the addition of a combination of the additives a) and b), or a) and c), or b) and c), or a) and b) and c) causes a stabilization of the serine endopeptidase.

Surprisingly, a preparation according to the invention has a higher stability in the liquid state and thus longer storage ability than the corresponding preparation in the absence of the additives mentioned.

To determine the stability of a preparation according to the invention, stability studies were carried out under accelerated stress conditions (see, for example, example 1). The stability of a preparation was investigated in the liquid state at a temperature of +52° C. Stability here is designated as the retention of the biological activity of a preparation. The stability of a preparation is the higher, the lower the loss of biological activity of the serine endopeptidase contained or the lower the number of degradation products of the serine endopeptidase contained.

It was observed that, for example, the serine endopeptidase F Xa in a preparation according to the invention in the liquid state has a loss of activity of less than 50% in a period of 48 hours at a storage temperature of +52° C. With the aid of the Arrhenius equation, the predicted stability of the preparation at other temperatures can be approximated using the stability of the preparation at +52° C. According to the Arrhenius equation, the stability of a sample at +2° C. compared to the stability at +52° C., roughly estimated, is increased approximately 32-fold, e.g., activities which are present after incubation at +52° C. for two days can still be expected at a storage temperature of +2° C. after approximately 64 days. For the determination of the loss of activity, the activity of the serine endopeptidase contained in the preparation is determined at an initial time point, to, e.g. immediately after production of the liquid preparation and then at least one later time point after storage of the liquid preparation at +52° C. over a defined period, preferably over a period of 48 hours. The loss of activity is determined by comparing the activity at $t_0$ (corresponds to 100%) with the activity after storage of the liquid preparation at +52° C. For the determination of the stability of a preparation which, for example, contains F Xa in enriched form, a suitable method includes measuring the cleavage of a chromogenic peptide substrate (see example 1).

One embodiment of the invention relates to a preparation which contains at least one serine endopeptidase and additionally ammonium acetate for stabilization. Such a preparation can additionally contain glycerol or additionally at least one amino acid from the group consisting of aspartic acid and its salts, glutamic acid and its salts, histidine and glycine.

Another embodiment of the invention relates to a preparation in which at least one serine endopeptidase and additionally at least one polyamino acid is present for stabilization. Such a preparation can additionally contain glycerol or additionally at least one amino acid from the group consisting of aspartic acid and its salts, glutamic acid and its salts, histidine and glycine.

If ammonium acetate is added to a preparation according to the invention, the ammonium acetate is preferably present in a final concentration of 25 to 1000 mM preferably 400 to 1000 mM, particularly preferably from 700 to 1000 mM.

If a polyamino acid is added to a preparation according to the invention, it can preferably be a polyamino acid from the group poly-L-glutamate and poly-L-aspartate. A polyamino acid is preferably present in a final concentration of 1 to 10 mM, preferably of 2 to 10 mM, particularly preferably of 2 to 5 mM.

Various embodiments of the preparation according to the invention can contain glycerol. If glycerol is added to a preparation according to the invention, the glycerol is preferably present in a final concentration of 0.5 to 50 percent by volume, preferably of 10 to 50 percent by volume, particularly preferably of 30 to 50 percent by volume.

Further embodiments of the preparation according to the invention can contain one or more amino acids from the group consisting of aspartic acid and its salts, glutamic acid and its salts, histidine and glycine. If an amino acid from the group histidine and glycine is added to a preparation according to the invention, histidine or glycine is preferably present in a final concentration of 10 to 250 mM, preferably of 25 to 200 mM, particularly preferably of 100 to 150 mM. If a preparation according to the invention contains an amino acid from the group aspartic acid and its salts and glutamic acid and its salts, the amino acid or its salt is preferably present in a final concentration of 10 to 1000 mM, preferably of 400 to 1000 mM, particularly preferably of 500 to 800 mM.

Surprisingly, it has been found that the addition of the amino acid lysine to a preparation which contains a serine endopeptidase, in contrast to the aforementioned amino acids, has a destabilizing effect, namely in any combination with one or more of the other additives according to the invention. No lysine should therefore be added to the preparations according to the invention. Hence, preferred preparations do not contain lysine.

Other embodiments of the preparation according to the invention can additionally contain one or more non-reducing sugars, preferentially from the group. sucrose and trehalose. If a nonreducing sugar is added to a preparation according to the invention, the sugar is preferably present in a final concentration of 20 to 500 mM, preferably of 50 to 400 mM, particularly preferably of 200 to 300 mM.

Still further additives can be added to a preparation according to the invention, such as, for example, polyethylene glycol, polyethylenimine, ionic or nonionic detergents (e.g. Triton® X-100, Tween® 20, Brij® 35), protease inhibitors, salts, such as, for example, $Ca^{2+}$ ions, heparins, albumins, preservatives with bactericidal, fungicidal or algicidal action (e.g. sodium azide, Kathon®, Mergal® etc.) and others, if the presence of such a further constituent does not decrease the stability of the preparation according to the invention or adversely affect the use of the preparation for a specific. purpose. Thus, it is necessary, in particular, in a preparation according to the invention which is intended for therapeutic use to avoid additives that are incompatible with therapeutic use.

The pH of a preparation according to the invention can be between 6.5 and 9.5, preferably between 7.4 and 8.5 and is particularly preferentially 8.0.

Additional embodiments of the preparation according to the invention contain a serine endopeptidase from the group of animal or human blood clotting factors, in particular a blood clotting factor from the group consisting of F II, F VII, F IX, F X, F XI and F XII or from the group of the activated blood clotting factors consisting of F IIa, F VIIa, F IXa, F Xa, F XIa and F XIIa. Furthermore, blood clotting factors of bovine origin are preferred.

Other embodiments of the preparation according to the invention contain a serine endopeptidase from the group of animal or human complement factors comprising complement factor C1r, C1s, complement factor D and complement factor I.

Other embodiments of the preparation according to the invention contain one or more of the serine endopeptidases which are listed in table 1. Additional embodiments contain a serine endopeptidase from the group consisting of chymotrypsin, trypsin, plasmin, acrosin, cathepsin G, plasma kallikrein, tissue kallikrein, pancreatic elastase, leucocyte elastase, C3/C5, convertase (classical), C3/C5 convertase (alternative), subtilisin, proteinase K, activated protein C, tissue plasminogen activator, urokinase plasminogen activator, furin, limulus clotting factor C, limulus clotting factor B, limulus clotting enzyme and snake venom factor V activator.

On account of the stabilizing action of the additives according to the invention, a preparation according to the invention is preferably made available in liquid form. Nonetheless, it is possible to lyophilize a preparation according to the invention. For this purpose, further stabilizers having cryoprotective action can optionally be added to the preparation according to the invention, such as, for example, polysaccharides such as mannitol, or proteins such as serum albumins, or polygelin, a gelatin derivative, or polyols.

A further subject of the present invention relates to processes for the production of a stabilized preparation according to the invention, which contains a serine endopeptidase in enriched form or to processes for the stabilization of a preparation comprising a serine endopeptidase. Among these is to be understood any process that ensures that additionally either a) ammonium acetate ($CH_3COONH_4$) or b) at least one polyamino acid or c) glycerol together with at least one amino acid from the group consisting of aspartic acid and its salts, glutamic acid and its salts, histidine and glycine or d) any desired combination of the additives a), b) and c) is added to a preparation which contains a serine endopeptidase. In another embodiment, an aqueous solution which contains a serine endopeptidase is mixed with one or more solutions which in each case contain one or more of the additives according to the invention. In another embodiment, an aqueous solution which contains a serine endopeptidase is mixed with one or more soluble solids which contain one or more of the additives according to the invention. In another embodiment, a lyophilisate which contains the serine endopeptidase can be dissolved in a reconstitution medium which already contains one or more of the additives according to the invention.

The present invention furthermore relates to the use of a) ammonium acetate and/or of b) polyamino acids and/or of c) glycerol in combination with at least one amino acid from the group consisting of aspartic acid and its salts, glutamic acid and its salts, histidine and glycine for the stabilization of a preparation which contains a serine endopeptidase.

A further subject of the present invention relates to the use of a stabilized preparation according to the invention which contains a serine endopeptidase in an analytical or diagnostic procedure or in a biocatalytic preparation process or for therapeutic purposes. Another use relates to the use of a stabilized preparation according to the invention as a test reagent in a test procedure for detecting an analyte or for the determination of a biological activity, such as, for example, of the clotting potential of a blood or plasma sample by means of a clotting time.

One embodiment of the present invention relates to the use of a stabilized preparation which contains subtilisin in a process for the preparation of detergents, for the preparation of animal food, in a process for leather production or for the separation of racemic mixtures in an organic synthesis process.

A further embodiment of the present invention relates to the use of a stabilized preparation which contains proteinase K in a process for the degradation of proteins in cell lysates and/or for the release of nucleic acids from cells or tissue or in a process for the identification of prion protein (scrapie etc).

A further embodiment of the present invention relates to the use of a stabilized preparation which contains furin in a process for the activation of enzymatically inactive precursors of proteolytic enzymes (zymogens).

Another use of a stabilized preparation according to the invention which contains at least one animal or human blood clotting factor, preferably from the group consisting of F II, F VII, F IX, F X, F XI and F XII and/or from the group consisting of F IIa, F VIIa, F IXa, F Xa, F XIa and F XIIa is the use as a test reagent in a test method for the determination of coagulation and/or fibrinolysis parameters in blood or plasma samples. An example of a use of this type of a preparation as a test reagent is the use of a preparation according to the invention which contains F Xa or F IIa (thrombin). Reagents comprising F Xa are used in various test procedures of clotting diagnosis, such as, for example, in test procedures for the determination or detection of antithrombin or heparin in patient samples. Embodiments of F Xa-based test procedures are described, for example, in the patent documents EP 216 179 B1 (example 2) and U.S. Pat. No. 5,308,755 (example 2). These procedures are based on the general test principle that a patient sample to be investigated is treated, inter alia, with an excess of F Xa and the F Xa-inhibiting action of the antithrombin or heparin contained in the sample is determined or detected by determining the residual activity of the F Xa after an incubation phase, for example using a chromogenic substrate. Reagents comprising F IIa (thrombin) are also used in various test procedures of coagulation diagnostics, such as, for example, in test procedures for the determination of the thrombin time, of the coagulable fibrin according to Clauss or alternatively in test procedures for the determination or detection of antithrombin or heparin cofactor II. These test procedures are essentially based on the fact that a defined amount of F IIa (thrombin) is added to a patient sample to be investigated and either the fibrin formation is measured in the form of a clotting time or the cleavage of a thrombin substrate is measured. One embodiment of an F IIa (thrombin) based test procedure for the determination of antithrombin is described, for example, in the patent document EP 216 179 B1 (example 1). On account of the lack of stability of conventional factor Xa or F IIa (thrombin) preparations, test reagents comprising F Xa and F IIa (thrombin) are mainly made available as lyophilisates. On account of the good stability of an F Xa or F IIa (thrombin) preparation according to the invention, the use of an F Xa preparation or F IIa (thrombin) preparation according to the invention as a test reagent which can be stored in the liquid state over a relatively long time is advantageous. Another example of the use of a preparation as a test reagent is the use of a preparation according to the invention which contains chymotrypsin in a process for the determination or detection of alpha$_1$-antichymotrypsin, an inhibitor of cellular proteases, as is described, for example, in the patent document EP 216 179 B1 (example 5).

A further subject of the present invention relates to the use of a stabilized preparation according to the invention which contains a serine endopeptidase as a control or standard solution in a test procedure intended for the quantitative or qualitative determination or detection of a serine endopeptidase. An example is the use of a stabilized preparation according to the invention as a control or standard which contains an animal or human blood clotting factor, preferably from the group consisting of F II, F VII, F IX, F X, F XI and F XII and/or from the group consisting of F IIa, F VIIa, F IXa, F Xa, F XIa and F XIIa, in a test procedure for the determination of the concentration or the activity of one of these factors. For example, a preparation according to the invention which contains F X or F Xa can be used as a standard or control in a process employed for determining the concentration or activity of F X or F Xa in patient samples. The activity or concentration which was determined in the patient sample by means of an appropriate activity assay or immunoassay is then compared with the activity or concentration of the standard or control determined in a parallel batch. The comparison of the measurements of the patient sample with the measurements of the standard or control, which contain a defined amount or activity of the serine endopeptidase, makes possible an assessment of the serine endopeptidase in the patient sample.

A further subject of the present invention relates to a test kit for use in a diagnostic test method. Such a test kit according to the invention, which can contain one or more test components, contains a preparation according to the invention comprising a serine endopeptidase, preferably in the form of a liquid preparation. Advantageously, a test kit additionally contains at least one further component which is necessary for carrying out of the diagnostic test method. In the case of a chromogenic test method for the determination or detection of an inhibitor of the serine endopeptidase (see F Xa, thrombin and alpha,-antichymotrypsin tests described above), preferably further reagents are present in a test kit, such as, for example, a reagent comprising a chromogenic substrate which is cleaved by the respective protease. A test kit for use in a procedure for the determination or detection of heparin in a patient sample can additionally contain a reagent which contains antithrombin. Another test kit for use in a procedure for the determination or detection of antithrombin in a patient sample can additionally contain a reagent which contains heparin. Furthermore, a test kit according to the invention can contain, for example, one or more buffer solutions, one or more calibration solutions, or one or more control solutions. Test kits which are intended for use in a procedure in which the biological activity of a parameter, for example the activity or presence of a protease inhibitor, is -determined in a plasma sample, can preferably contain one or more calibration plasmas or one or more control plasmas, such as, for example, normal plasma and/or abnormal plasma.

A further subject of the present invention relates to the use of a stabilized preparation according to the invention as a therapeutic or for the production of a therapeutic. The use of preparations which contain at least one animal or human blood clotting factor, preferably from the group consisting of F II, F VII, F IX, F X, F XI and F XII and/or from the group of the corresponding activated blood clotting factors for the treatment of coagulation disorders or for the production of a corresponding therapeutic is preferred. A preparation according to the invention comprising F X and/or F Xa is suitable, for example, for the treatment of patients with defects of the clotting system or for the production of a corresponding therapeutic.

The following working examples serve for the illustration of the process according to the invention and are not to be understood as a restriction.

DESCRIPTION OF FIGURES

Figure 1:
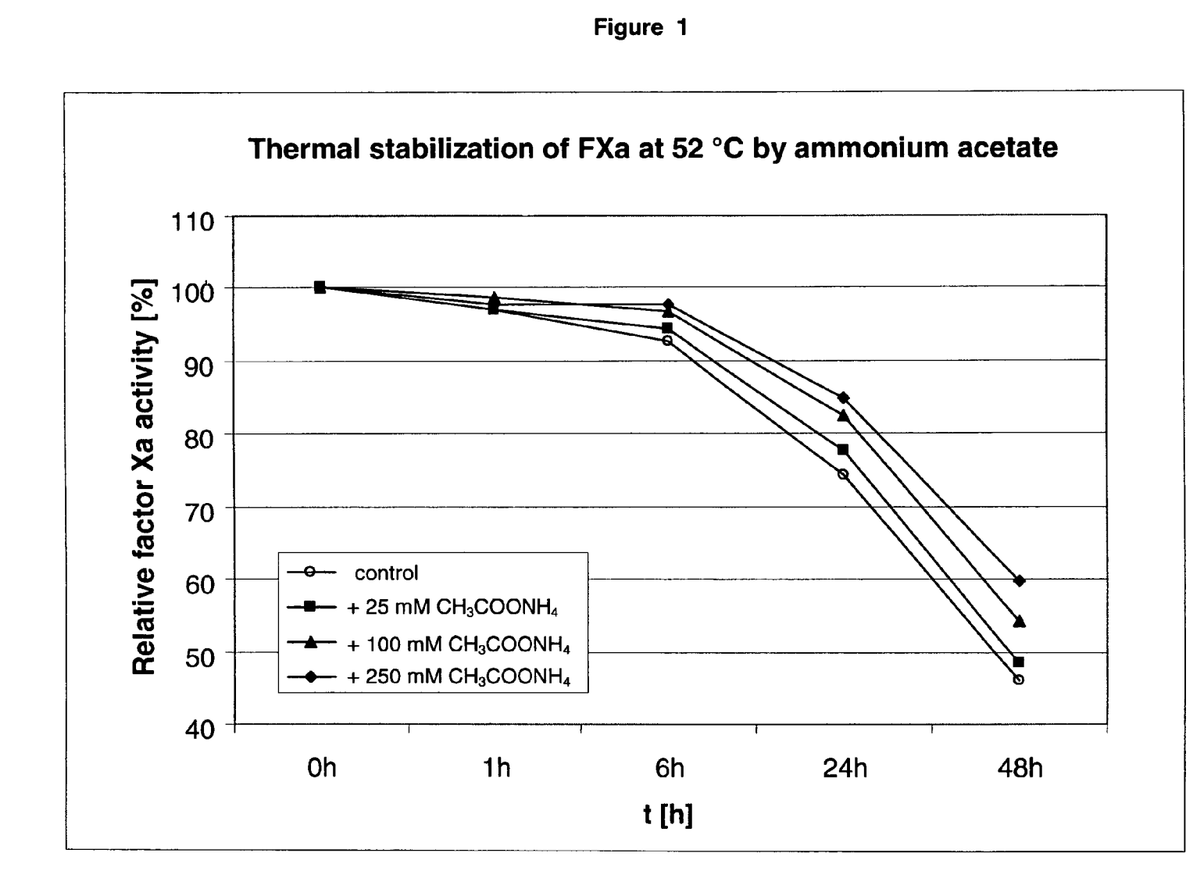
FIG. 1 is a graphic representation of the stabilizing effect of various ammonium acetate concentrations in an F Xa liquid preparation which was incubated at +52° C. for 48 hours.

FIG. 1

FIG. 1 is a graphic representation of the stabilizing effect of various ammonium acetate concentrations in an F Xa liquid preparation which was incubated at +52° C. for 48 hours. The F Xa activity contained in the samples was determined at the times t=0; 1 h; 6 h; 24 h and 48 h by means of the cleavage of a chromogenic F Xa substrate. The activity measured at the time t=0 was set equal to 100%. The activities measured at later times are indicated relative to the activity at t=0. It can clearly be seen that in the presence of ammonium acetate in the F Xa liquid preparation the thermal stability of F Xa is increased compared to the control without ammonium acetate. The increase. in the stability is concentration-dependent, i.e. the higher the ammonium acetate concentration the greater the stabilizing effect.

Figure 2:
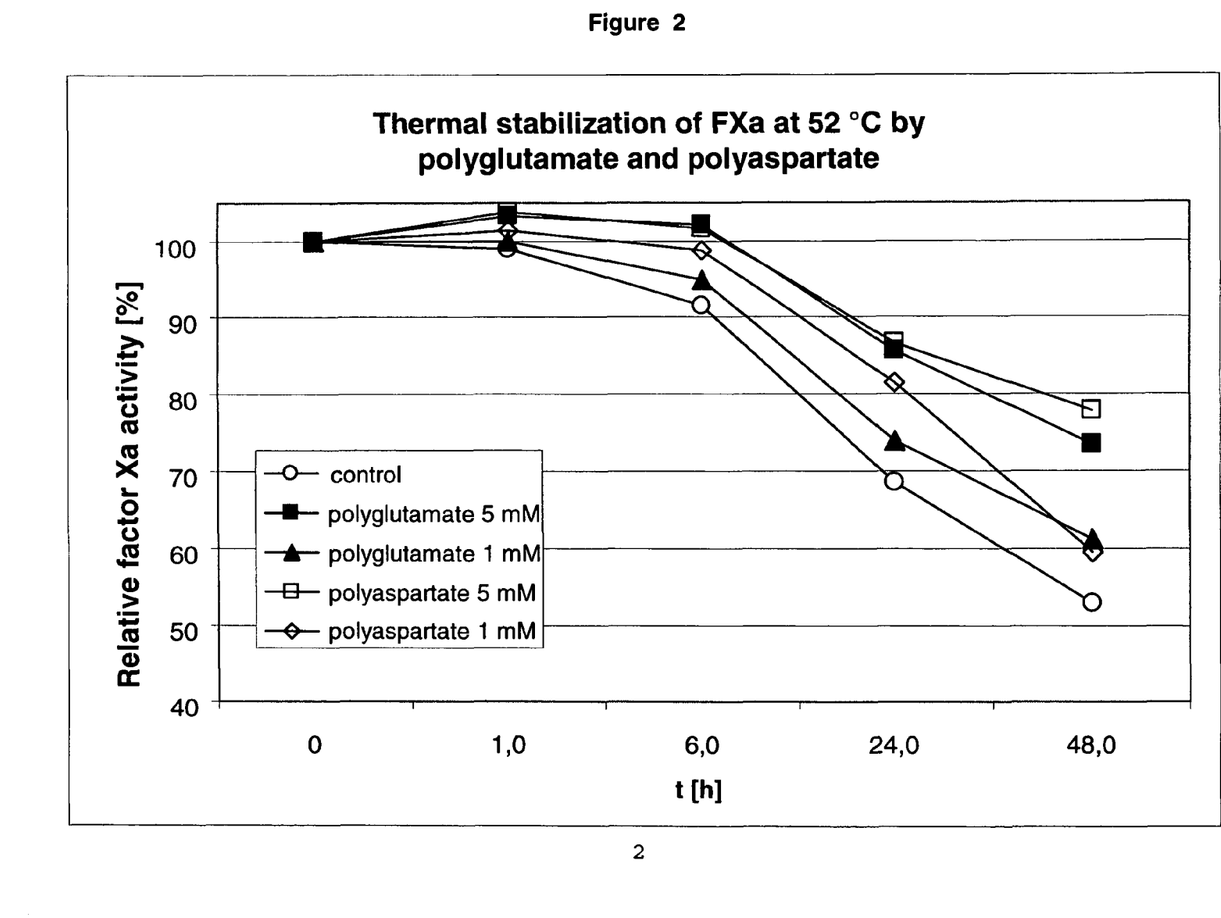
FIG. 2 is a graphic representation of the stabilizing effect of various concentrations of the polyamino acids polyglutamate and polyaspartate in an F Xa liquid preparation which was incubated at +52° C. for 48 hours.

FIG. 2

FIG. 2 is a graphic representation of the stabilizing effect of various concentrations of the polyamino acids polyglutamate and polyaspartate in an F Xa liquid preparation which was incubated at +52° C. for 48 hours. The F Xa activity contained in the samples was measured at the times t=0; 1 h; 6 h; 24 h and 48 h. The activity measured at the time t=0 was set equal to 100%. The activities measured at later times are indicated relative to the activity at t=0. It can clearly be seen that in the presence of a polyamino acid in the F Xa liquid preparation the thermal stability of F Xa is increased compared to the control without polyamino acid. The increase in the stability is concentration-dependent, i.e. the higher the polyamino acid concentration the greater the stabilizing effect.

Figure 3:
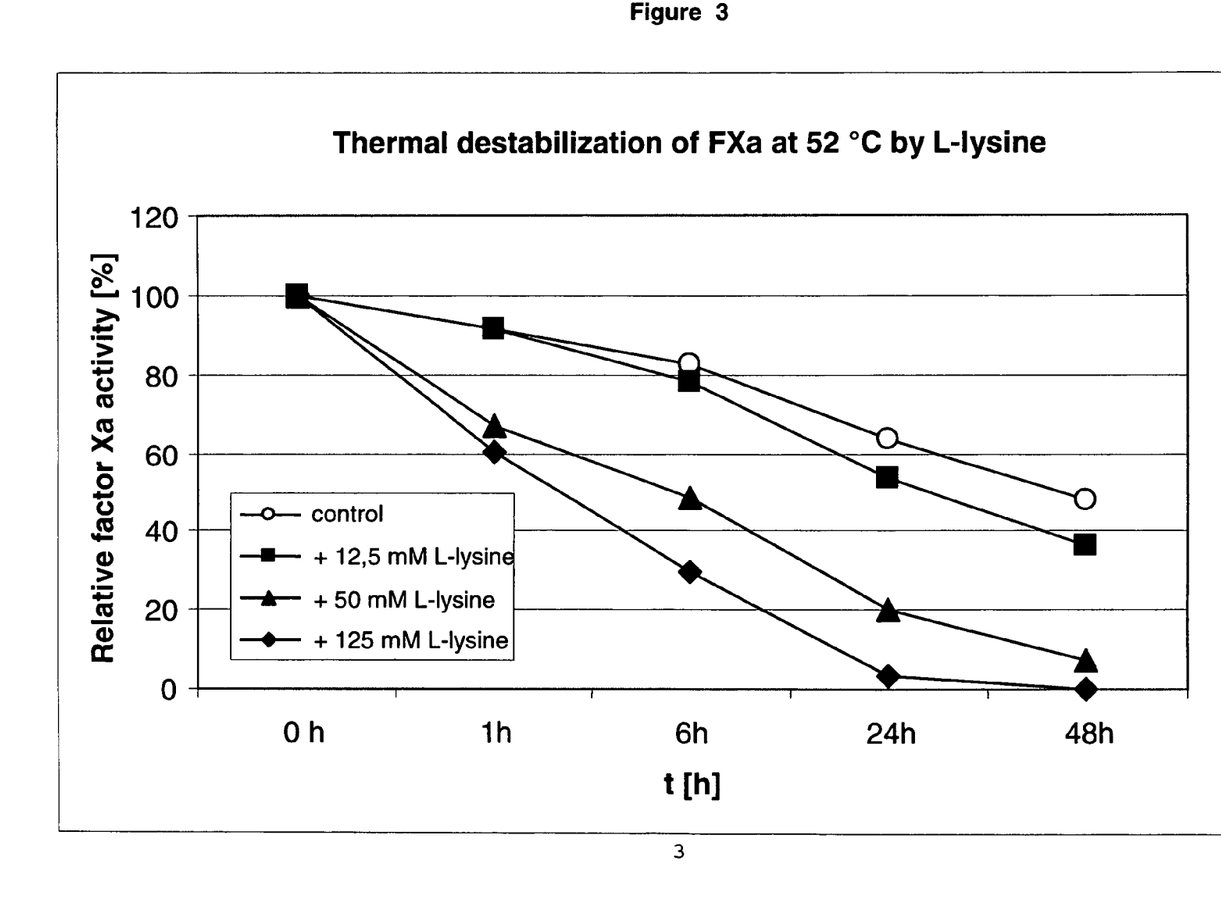
FIG. 3 documents a comparison experiment and is a graphic representation of the destabilizing effect of various concentrations of the amino acid lysine in an F Xa liquid preparation which was incubated at +52° C. for 48 hours.

FIG. 3

FIG. 3 documents a comparison experiment and is a graphic representation of the destabilizing effect of various concentrations of the amino acid lysine in an F Xa liquid preparation which was incubated at +52° C. for 48 hours. It can clearly be seen that in the presence of L-lysine in the F Xa liquid preparation the thermal stability of F Xa is decreased compared to the control without L-lysine. The decrease in the stability is concentration-dependent, i.e. the higher the L-lysine concentration, the greater the destabilizing effect. In contrast to the stabilizing substances according to the invention, the addition of L-lysine to a liquid F Xa preparation not only has no stabilizing action, but even causes the opposite, namely a destabilization of F Xa.

Figure 4:
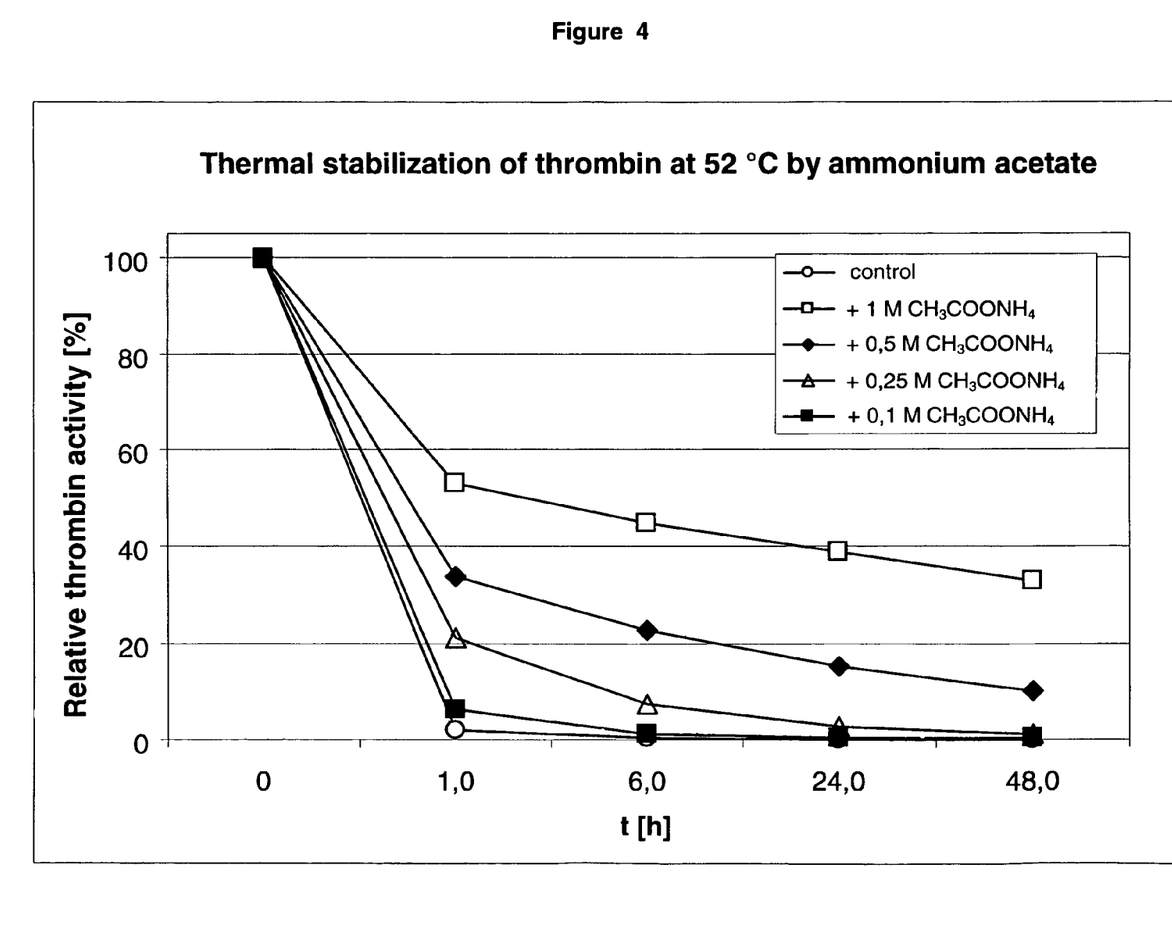
FIG. 4 is a graphic representation of the stabilizing effect of various ammonium acetate concentrations in a thrombin liquid preparation which was incubated at +52° C. for 48 hours.

FIG. 4

FIG. 4 is a graphic representation of the stabilizing effect of various ammonium acetate concentrations in a thrombin liquid preparation which was incubated at +52° C. for 48 hours. The thrombin activity contained in the samples was measured at the times t=0; 1 h; 6 h; 24 h and 48 h. The activity measured at the time t=0 was set equal to 100%. The activities measured at later times are indicated relative to the activity at t=0. It can clearly be seen that in the presence of ammonium acetate in the thrombin liquid preparation the thermal stability of thrombin is increased compared to the control without ammonium acetate. The increase in the stability is concentration-dependent, i.e. the higher the ammonium acetate concentration the greater the stabilizing effect.

EXAMPLES

Example 1

Preparation of F Xa Liquid Preparations According to the Invention by Addition of Ammonium Acetate, Poly-Amino Acids or Glycerol and Amino Acids and their Thermostability Under Stress Conditions To obtain human F X, a prothrombin complex lyophilisate which had been obtained from human plasma was dissolved and the proteins of the prothrombin complex preparatiorr were precipitated by addition of 25% (w/v) ammonium sulfate. The precipitated protein mixture was separated from the supernatant by centrifugation, resuspended and dialyzed against trisodium citrate dihydrate buffer (4.0 g/l), pH 6.5. The dialyzate was subsequently chromatographed on a dextran sulfate-Sepharose material. The F X was separated from the remaining protein components of the prothrombin complex with the aid of a sodium chloride gradient in trisodium citrate dihydrate buffer (pH 6.5). The fractions comprising F X were combined and dialyzed against the 10-fold volume of a buffer (pH 8.0) comprising 6 g/l of trishydroxymethylaminomethane and 0.6 g/l of calcium chloride dihydrate. The activation of F X to F Xa was carried out by addition of 5 mg of RVV (Russell's viper venom) per liter of factor Xa pool and subsequent incubation at room temperature overnight. The F Xa prepared in this way was concentrated by ammonium sulfate precipitation and taken up in 30 g/l of trishydroxymethylaminomethane, 60 g/l of sodium chloride (pH 8.0). For storage, the protein solution comprising F Xa was subsequently lyophilized. The lyophilisate contained 2 U of F Xa per mg, the unit 1 U corresponding to the amount of enzyme which is contained in 1 ml of normal plasma.

2 mg in each case of the F Xa lyophilisate were dissolved in 5.4 ml of buffer 1 (19 mmol/l of tris/HCl, 67 mmol/l of NaCl, 81 mmol/l of $CaCl_2$, pH 8.0) or in buffer 1 which additionally contained one or more stabilizing substances according to the invention, and subsequently treated with 1.35 µl of Fragmin®, a low molecular weight heparin (1000 U/ml; Pharmacia, Kalamazoo, USA), and with 31.7 µl of aprotinin (1.4 mg/ml). The final concentration of the stock solution of F Xa was 0.73 U/ml.

To investigate the stability of the preparations according to the invention under accelerated stress conditions, two samples in each case were prepared from each of the F Xa liquid preparations according to the invention, which contained one or more of the stabilizing substances according to the invention in a specific concentration. All F Xa samples according to the invention and the F Xa control samples, which contained F Xa in the same buffer, but without addition of a stabilizing substance according to the invention, were incubated for at least 48 hours at +52° C. in a thermoblock.

To determine the F Xa activity in a sample, 80 µl aliquots in each case were taken at the time t=0, i.e. immediately after the dissolution of the F Xa lyophilisate in buffer 1 and before warming to +52° C., and then after various incubation times at +52° C., and the F Xa activity was determined on the automatic coagulation analyzer Sysmex® CA-7000 (Sysmex Corporation, Kobe, Japan). For this, the respective aliquot was first diluted with 40 µl of buffer 1 by the coagulation analyzer. After an incubation for 12 seconds at +37° C., 80 µl of substrate reagent (Z-D-Leu-Gly-Arg-ANBA-methylamide, 1.5 mM) were added to each sample and the mixture was subsequently incubated at +37° C. for a further 84 seconds. The F Xa-dependent generation of the chromophore ANBA (5-amino-2-nitro-benzoic acid) was recorded by the automatic coagulation analyzer at a temperature of +37° C. and a wavelength of 405 nm and the change in extinction in $\Delta OD$/min was determined therefrom as a measure of the F Xa activity. The results which were determined concurrently for the two samples of a specific F Xa liquid preparation were averaged.

The stabilizing effects of various combinations of stabilizers according to the invention in an F Xa liquid preparation are shown in tables 2 and 3. At the time t=0, a chromogenic F Xa activity test was carried out as described above and the F Xa activity was quantified by means of the extinction change in $\Delta OD$/min. At 24 and 48 hours after the beginning of the incubation at +52° C., the remaining F Xa activity of each test batch was determined and the percentage decrease Was determined compared to the activity at the time t=0. The ratio of the percentage decrease in the signal of the control sample without stabilizer according to the invention ("control") and the percentage decrease in the signal of a preparation according to the invention ("sample"), at the time t=24 h or t=48 h (decrease in activity control/decrease in activity sample), illustrates the stabilizing effect of a composition according to the invention. Ratios>1 indicate a stabilizing effect of the substance or substance combination added; ratios<1 would indicate a destabilizing effect of the added substance or substance combination; a ratio=1 indicates that an added substance or substance combination has no effect on the stability.

As can be seen from table 2, the F Xa activity in the presence of a combination of glycerol with sodium aspartate and/or with sodium glutamate is significantly more stable than in the presence of the individual additives. The addition of ammonium acetate further increases stability.

It is evident from table 3 that the F Xa activity is more stable in the presence of ammonium acetate and particularly in the presence of ammonium acetate together with sodium aspartate and/or sodium glutamate or together with glycerol than its stability in the absence of ammonium acetate.

Further results of the stability studies are shown in FIGS. 1-3 and the associated descriptions of the figures.

TABLE 2

Stabilization of F Xa by the addition of a combination of glycerol and one or more amino acids

| F Xa preparation | Signal [dOD/min] Time 0 h | Signal [dOD/min] Time 24 h | Percentage decrease in signal [%] | Signal [dOD/min] Time 48 h | Percentage decrease in signal [%] | Decrease in activity of control / Decrease in activity of sample |
|---|---|---|---|---|---|---|
| Control (F Xa in buffer 1) | 1.413 | 0.885 | 37.4 | 0.703 | 50.2 | 1 |
| +33% glycerol | 1.532 | 1.178 | 23.1 | 1.001 | 34.7 | 1.45 |
| +200 mM sodium glutamate | 1.624 | 1.355 | 16.4 | 1.157 | 28.6 | 1.76 |
| +200 mM sodium aspartate | 1.635 | 1.377 | 15.8 | 1.201 | 26.5 | 1.89 |
| +33% glycerol +200 mM sodium glutamate | 1.759 | 1.590 | 9.6 | 1.460 | 17.0 | 2.95 |
| +33% glycerol +200 mM sodium aspartate | 1.865 | 1.682 | 9.8 | 1.554 | 16.7 | 3.00 |
| +33% glycerol +200 mM sodium aspartate +200 mM sodium glutamate | 2.108 | 2.015 | 4.4 | 1.915 | 9.2 | 5.46 |
| +33% glycerol +200 mM sodium glutamate +300 mM ammonium acetate | 1.894 | 1.764 | 6.9 | 1.666 | 12.0 | 4.18 |
| +33% glycerol +200 mM sodium aspartate +300 mM ammonium acetate | 1.883 | 1.779 | 5.5 | 1.689 | 10.3 | 4.87 |
| +33% glycerol +200 mM sodium aspartate +200 mM sodium glutamate +300 mM ammonium acetate | 2.069 | 1.975 | 4.5 | 1.880 | 9.1 | 5.52 |

TABLE 3

Stabilization of F Xa by addition of ammonium acetate

| F Xa preparation | Signal [dOD/min] Time 0 h | Signal [dOD/min] Time 24 h | Percentage decrease in signal [%] | Signal [dOD/min] Time 48 h | Percentage decrease in signal [%] | Decrease in activity of control Decrease in activity of sample |
|---|---|---|---|---|---|---|
| Control (F Xa in buffer 1) | 1.413 | 0.885 | 37.4 | 0.703 | 50.2 | 1 |
| +300 mM ammonium acetate | 1.513 | 1.064 | 29.7 | 0.909 | 39.9 | 1.26 |
| +300 mM ammonium acetate +200 mM sodium glutamate | 1.702 | 1.486 | 12.7 | 1.322 | 22.3 | 2.25 |
| +300 mM ammonium acetate +200 mM sodium aspartate | 1.711 | 1.489 | 13.0 | 1.329 | 22.3 | 2.25 |
| +300 mM ammonium acetate +200 mM sodium aspartate +200 mM sodium glutamate | 1.778 | 1.666 | 6.3 | 1.526 | 14.2 | 3.54 |
| +300 mM ammonium acetate +33% glycerol | 1.658 | 1.385 | 16.5 | 1.237 | 25.4 | 1.98 |

Example 2

Preparation of F Xa Liquid Preparations by Addition of L-Lysine and their Thermostability Under Stress Conditions (Comparison Experiment)

In analogy to the experiments in example 1, a comparison experiment was carried out in which F Xa preparations were produced by the use of buffer 1 which contained different concentrations of the amino acid L-lysine. The destabilizing action of L-lysine is shown in FIG. 3 and the associated description of the figures.

Example 3

Production of Thrombin Liquid Preparations According to the Invention by Addition of Ammonium Acetate A commercially available thrombin lyophilisate was used. This was a lyophilized bovine thrombin with addition of heparin, mannitol, NaCl and aprotinin. The lyophilisate was dissolved in buffer 2 (12 g/l of tris, 9 g/l of NaCl, pH 8.2) or in buffer 2 which additionally contained ammonium acetate in various concentrations. The thrombin preparations thus obtained contained approximately 4 to 5 IU of thrombin per ml.

To investigate the stability of the thrombin preparations under accelerated stress conditions, two samples in each case were prepared from each of the thrombin liquid preparations according to the invention which contained ammonium acetate. All thrombin samples according to the invention and the thrombin control samples which contained thrombin in the same buffer without addition of ammonium acetate were incubated for at least 48 hours at +52° C. in a thermoblock.

To determine thrombin activity in a sample, 175 µl aliquots were in each case taken at time t=0, i.e. immediately after dissolution of the thrombin lyophilisate in buffer 2 and before warming to +52° C. and then after various incubation times at +52° C., and the thrombin activity was determined on the automatic coagulation analyzer Sysmex® CA-7000 (Sysmex Corporation, Kobe, Japan). For this determination, the respective aliquot was first mixed with 24 µl of reaction buffer by the coagulation analyzer. After incubation for 180 seconds at +37° C., 33 µl of substrate reagent (Tos-Gly-Pro-Arg-ANBA-isopropylamide, 2 mM) were added to each sample. The thrombin-dependent generation of the chromophore ANBA (5-amino-2-nitro-benzoic acid) was recorded at a temperature of +37° C. and a wavelength of 405 nm by the automatic coagulation analyzer and the change in extinction was determined in ΔOD/min as a measure of the thrombin activity. The results, which were determined in parallel for the two samples of a specific thrombin liquid preparation, were averaged.

The results of the stability study are shown in FIG. 4 and the associated description of the figures.

We claim:

1. A preparation for stabilizing serine endopeptidases, comprising at least one serine endopeptidase and an effective amount of glycerol together with at least one amino acid selected from the group consisting of aspartic acid and its salts, glutamic acid and its salts, histidine, and glycine.

2. The preparation of claim 1, wherein glycerol is present in a final concentration of 0.5 to 50 percent by volume.

3. The preparation of claim 1, wherein the amino acid is selected from the group consisting of histidine, and glycine, and wherein the amino acid is present in a final concentration of 10 to 250 mM.

4. The preparation of claim 1, wherein the amino acid is selected from the group consisting of aspartic acid and its salts, and glutamic acid and its salts, and wherein the amino acid is present in a final concentration of 10 to 1000 mM.

5. The preparation of claim 1 further comprising at least one nonreducing sugar.

6. The preparation of claim 1, wherein the serine endopeptidase is an animal or human blood clotting factor selected from the group consisting of F II, F VII, F IX, F X, F XI, F XII, F IIa, F VIIa, F IXa, F Xa, F XIa, and F XIIa.

7. The preparation of claim 1, wherein the serine endopeptidase is an animal or human complement factor selected from the group consisting of C1r, C1s, complement factor D, and complement factor I.

8. The preparation of claim 1, wherein the serine endopeptidase is selected from the group consisting of chymotrypsin, trypsin, plasmin, acrosin, cathepsin G, plasma kallikrein, tissue kallikrein, pancreatic elastase, leucocyte elastase, C3/C5 convertase (classical), C3/C5 convertase (alternative), subtilisin, proteinase K, activated protein C, tissue plasminogen activator, urokinase plasminogen activator, furin, limulus clotting factor C, limulus clotting factor B, limulus clotting enzyme, and snake venom factor V activator.

9. The preparation of claim 1, wherein the preparation is liquid.

10. The preparation of claim 1, wherein no lysine is added to the preparation.

11. The preparation of claim 1, wherein glycerol is present in a final concentration of 10 to 50 percent by volume.

12. The preparation of claim 1, wherein glycerol is present in a final concentration of 30 to 50 percent by volume.

13. The preparation of claim 1, wherein the amino acid is selected from the group consisting of aspartic acid and its salts and glutamic acid and its salts, and wherein the amino acid is present in a final concentration of 400 to 1000 mM.

14. The preparation of claim 1, wherein the amino acid is selected from the group consisting of aspartic acid and its salts and glutamic acid and its salts, and wherein the amino acid is present in a final concentration of 500 to 800 mM.

15. A preparation for stabilizing serine endopeptidases, comprising at least one serine endopeptidase and an effective amount of glycerol together with at least one of sodium aspartate and sodium glutamate.

16. A preparation for stabilizing serine endopeptidases, comprising at least one serine endopeptidase and an effective amount of ammonium acetate and glycerol together with at least one of sodium aspartate and sodium glutamate.

17. A preparation for stabilizing serine endopeptidases, comprising at least one serine endopeptidase and an effective amount of ammonium acetate.

18. The preparation of claim 17, wherein ammonium acetate is present in a final concentration of 25 to 1000 mM.

19. The preparation of claim 17 further comprising at least one nonreducing sugar.

20. The preparation of claim 17, wherein the serine endopeptidase is an animal or human blood clotting factor selected from the group consisting of F II, F VII, F IX, F X, F XI, F XII, F IIa, F VIIa, F IXa, F Xa, F XIa, and F XIIa.

21. The preparation of claim 17, wherein the preparation is liquid.

22. The preparation of claim 17, wherein ammonium acetate is present in a final concentration of 400 to 1000 mM.

23. The preparation of claim 17, wherein ammonium acetate is present in a final concentration of 700 to 1000 mM.

24. A preparation for stabilizing serine endopeptidases, comprising at least one serine endopeptidase and an effective amount of at least one polyamino acid.

25. The preparation of claim 24, wherein at least one polyamino acid is selected from the group consisting of poly-L-glutamate and poly-L-aspartate.

26. The preparation of claim 25, wherein the polyamino acid is present in a final concentration of 1 to 10 mM.

27. The preparation of claim 24 further comprising at least one nonreducing sugar.

28. The preparation of claim 24, wherein the serine endopeptidase is an animal or human blood clotting factor selected from the group consisting of F II, F VII, F IX, F X, F XI, F XII, F IIa, F VIIa, F IXa, F Xa, F XIa, and F XIIa.

29. The preparation of claim 24, wherein the preparation is liquid.

30. The preparation of claim 24, wherein the polyamino acid is present in a final concentration of 2 to 10 mM.

31. The preparation of claim 24, wherein the polyamino acid is present in a final concentration of 2 to 5 mM.

* * * * *

UNITED STATES PATENT AND TRADEMARK OFFICE
CERTIFICATE OF CORRECTION

PATENT NO. : 8,124,737 B2  Page 1 of 1
APPLICATION NO. : 11/709747
DATED : February 28, 2012
INVENTOR(S) : Lichte et al.

It is certified that error appears in the above-identified patent and that said Letters Patent is hereby corrected as shown below:

Title page, item (73), Assignee, "Seimens Healthcare Diagnostics Products GmbH" should read --Siemens Healthcare Diagnostics Products GmbH--.

Signed and Sealed this
Eighth Day of May, 2012

David J. Kappos
*Director of the United States Patent and Trademark Office*